(12) United States Patent
Wilkinson

(10) Patent No.: US 6,926,702 B1
(45) Date of Patent: Aug. 9, 2005

(54) DIAPER WITH LEGS

(76) Inventor: Lisa Diane Crislip Wilkinson, 373 Spring St., Spencer, TN (US) 38585

( * ) Notice: Subject to any disclaimer, the term of this patent is extended or adjusted under 35 U.S.C. 154(b) by 0 days.

(21) Appl. No.: 10/791,849

(22) Filed: Mar. 4, 2004

(51) Int. Cl.$^7$ ............................................. A61F 13/15
(52) U.S. Cl. .................. 604/385.01; 604/394
(58) Field of Search ...................... 604/385.01, 385.03, 604/385.21, 385.24, 385.25, 385.226, 385.27, 604/385.29, 385.3, 394, 396; 2/400–408

(56) References Cited

U.S. PATENT DOCUMENTS

| | | | |
|---|---|---|---|
| 1,939,257 A * | 12/1933 | Erlanger ........................ | 2/404 |
| 2,034,312 A * | 3/1936 | Betty ............................ | 2/228 |
| 2,391,641 A * | 12/1945 | O'Hern ......................... | 2/407 |
| 2,599,769 A * | 6/1952 | MacRae et al. ................ | 2/228 |
| 2,763,009 A * | 9/1956 | Blatt ........................... | 450/104 |
| 2,827,638 A * | 3/1958 | Scharf .......................... | 2/212 |
| 3,678,514 A * | 7/1972 | Safrit ........................... | 2/212 |
| 3,714,946 A * | 2/1973 | Rudes ......................... | 604/394 |
| 4,673,402 A * | 6/1987 | Weisman et al. ........... | 604/368 |
| 4,870,958 A * | 10/1989 | Webster ...................... | 602/67 |
| 4,936,840 A | 6/1990 | Proxmire | |
| 5,136,727 A * | 8/1992 | Brisco .......................... | 2/409 |
| 5,435,014 A * | 7/1995 | Moretz et al. ................ | 2/403 |
| 5,876,394 A * | 3/1999 | Rosch et al. ................ | 604/393 |
| 5,916,206 A | 6/1999 | Otsubo et al. | |
| 5,921,974 A * | 7/1999 | Kikuchi ................ | 604/385.24 |
| 5,989,236 A * | 11/1999 | Roe et al. ............... | 604/385.04 |
| 6,108,823 A * | 8/2000 | Danes ........................... | 2/403 |
| 6,115,847 A * | 9/2000 | Rosch et al. .................. | 2/238 |
| 6,156,024 A | 12/2000 | Schulte et al. | |
| 6,210,386 B1 | 4/2001 | Inoue | |
| 6,289,519 B1 * | 9/2001 | Murakami et al. ............. | 2/400 |
| 6,293,936 B1 * | 9/2001 | Otsubo ....................... | 604/396 |
| 6,293,937 B2 * | 9/2001 | Matsushita et al. ......... | 604/396 |
| 6,308,339 B1 * | 10/2001 | Murakami et al. ............. | 2/400 |
| 6,328,724 B1 | 12/2001 | Ronnberg et al. | |
| 6,336,923 B1 * | 1/2002 | Fujioka et al. .............. | 604/394 |
| 6,376,740 B1 * | 4/2002 | Suzuki et al. ............... | 604/358 |
| 6,482,196 B1 | 11/2002 | Hisada | |
| 6,520,944 B1 | 2/2003 | Jonbrink | |
| 6,582,412 B2 * | 6/2003 | Christoffel et al. .... | 604/385.01 |

(Continued)

FOREIGN PATENT DOCUMENTS

JP    11-290377    10/1996

(Continued)

Primary Examiner—Larry I. Schwartz
Assistant Examiner—Michael G. Bogart
(74) Attorney, Agent, or Firm—Richard C. Litman

(57) ABSTRACT

The diaper with legs of the present invention is a lower torso garment worn by a user to retain excreted waste matter. The diaper may have fasteners to close the waist and legs, or may be of the pull-on type. The diaper includes a flat sheet wrapped around the torso with legs extending from the sides of the sheet. A front waist arch and a rear waist arch are disposed at an upper portion of the edges of the sheet. The arches extend the height of the diaper in front and back. An elastic material is disposed at the waist arches, at the junction between the legs and the central portion of the diaper, and at the end of the legs. The elastic material disposed at the end of the legs and at the junction between the legs and the central portion provide double leak protection at the legs.

13 Claims, 3 Drawing Sheets

U.S. PATENT DOCUMENTS

| | | | |
|---|---|---|---|
| 6,626,883 B2 * | 9/2003 | Wada et al. | 604/396 |
| 6,666,851 B2 * | 12/2003 | Otsubo et al. | 604/385.201 |
| 6,761,712 B2 * | 7/2004 | Otsubo et al. | 604/396 |
| 2002/0052588 A1 * | 5/2002 | Otsubu | 604/385.01 |
| 2002/0165518 A1 | 11/2002 | Datta et al. | |
| 2002/0183706 A1 * | 12/2002 | Valentin et al. | 604/385.01 |
| 2003/0149418 A1 | 8/2003 | Katz | |
| 2003/0158532 A1 | 8/2003 | Magee et al. | |
| 2003/0164136 A1 | 9/2003 | Klofta et al. | |
| 2003/0181883 A1 | 9/2003 | Olson et al. | |
| 2003/0199841 A1 | 10/2003 | Ashton et al. | |
| 2003/0199844 A1 | 10/2003 | La Von et al. | |
| 2003/0208171 A1 | 11/2003 | Zehner et al. | |
| 2003/0212378 A1 | 11/2003 | Kuen et al. | |
| 2003/0220626 A1 | 11/2003 | Karami | |
| 2003/0225385 A1 | 12/2003 | Glaug et al. | |
| 2003/0229327 A1 | 12/2003 | Imsangjan et al. | |
| 2003/0229329 A1 * | 12/2003 | Mercier et al. | 604/394 |
| 2004/0002690 A1 | 1/2004 | Miyamoto | |
| 2004/0002691 A1 | 1/2004 | Popp et al. | |

FOREIGN PATENT DOCUMENTS

| | | | | |
|---|---|---|---|---|
| JP | 2003-38554 | | 2/2003 | |
| JP | 2003-88262 | | 3/2003 | |
| JP | 2003-199778 | | 7/2003 | |
| JP | 2003-210518 | | 7/2003 | |
| WO | WO 91/08725 | * | 6/1991 | A61F 13/15 |

* cited by examiner

DIAPER WITH LEGS

BACKGROUND OF THE INVENTION

1. Field of the Invention

The present invention relates to disposable diapers, and more particularly to a diaper with legs. The diaper may have reclosable fasteners about the waist and legs, or may be of the pull-on type without fasteners.

2. Description of the Related Art

Absorbent articles for the lower torso, such as diapers, pull-on diapers and pull-on pants, are used to capture waste matter for infants and those who cannot control their bodily functions. Absorbent articles have made life cleaner and easier for those who wear the articles and their caregivers. These absorbent articles, however, are not entirely problem free. There are times when body exudates seep through the openings of the absorbent article, such as at the leg openings and the waist opening. A diaper is therefore desired that can contain waste matter that may leak out the openings of the diaper.

A number of pant-like absorbent articles have been developed to aid is retaining waste matter excreted by the body. U.S. Patent Publication No. 2002/0165518, published on Nov. 7, 2002, describes a pant-like, prefastened, disposable absorbent article that reduces leakage when worn as pants rather than a diaper. In one embodiment, the absorbent article has a pair of elastic leg members that are adapted to fit about the legs of a wearer. The leg members maintain contact with the legs and reduce or eliminate leaks. The absorbent article has an absorbent core with a pocket defined therein to receive and retain body exudates. Additionally, the absorbent article may have a containment flap disposed near the pocket to provide a barrier to the lateral flow of body excretions.

U.S. Patent Publication No. 2003/0181883, published on Sep. 25, 2003, describes a garment-like absorbent article. The article is a pant-like article that functions like underwear. The article has a pair of leg openings. The length of the outer cover of the article, measured from the front waist edge to the rear waist edge can be shorter then other bulkier garments so the article can be worn without being visible over the waistline of lower torso garments.

U.S. Pat. No. 5,916,206, issued to Ostubo et al. on Jun. 29, 1999, describes an absorbent pant-like undergarment that utilizes elastic elements to prevent leaks. The pants-type undergarment has a pair of leg openings to configure the garment into pants or a brief-like shape. U.S. Pat. No. 6,210,386, issued to Inoue on Apr. 3, 2001, describes a disposable pull-on, pant-type undergarment having elastic auxiliary flaps to secure the garment to the waist and aid in disposal of the garment. U.S. Pat. No. 6,328,724, issued to Ronnberg et al. on Dec. 11, 2001, describes an absorbent article having longitudinal side flaps for retaining liquid within the absorbent article.

U.S. Pat. No. 6,482,196, issued to Hisada on Nov. 19, 2002, describes disposable undergarment pants combined with a belly protector. The undergarment has a front body joined to a rear body to define both a tubular waist configuration at the top of the undergarment and leg openings at the bottom of the undergarment. Elastic is integrated into both the belly protector and the pants section of the undergarment.

U.S. Patent Publication No. 2003/0199841, published on Oct. 23, 2003 to Ashton et al., describes an absorbent article having article retention zones dependent on static friction. One embodiment shows a pant-like absorbent article. Japanese Patent No. 2003-210518, published on Jul. 29, 2003, shows a disposable pant-type diaper having legs. Japanese Patent No. 2003-38554, published on Feb. 5, 2003, shows a pant-type disposable diaper having a penis-receiving zone.

Some absorbent articles have been developed that utilize leg cuffs. U.S. Patent Publication No. 2003/0208171, published on Nov. 6, 2003, describes an absorbent article with self-forming seals. The article fits like pants having seals at natural body hinge points of a wearer and in-captured elastic leg cuffs. The leg cuffs extend from the absorbent core of the diaper article and provide targeted stretch and recovery as the leg moves.

U.S. Patent Publication No. 2003/0158532, published on Aug. 21, 2003, describes a disposable absorbent article for the lower body. The article may have barrier cuffs or gasketing leg cuffs disposed on a portion of the article that faces the body. The cuffs may help in preventing leaks. U.S. Patent Publication No. 2004/0002690, published on Jan. 1, 2004, describes a disposable absorbent article having elasticized outer leg cuffs. The gasket cuff contains a sleeve that holds elastic material to provide a seal with the leg.

U.S. Pat. No. 6,156,024, issued to Schulte et al. on Dec. 5, 2000, describes an absorbent article having lotioned leg cuffs. Japanese Patent No. 2003-88262, published on Mar. 25, 2003, describes a pet diaper. Japanese Patent No. 11-290377, published on Oct. 26, 1999, shows a pants-shaped disposable diaper having elastic members on a front panel and a back panel. Japanese Patent No. 2003-199778, published on Jul. 15, 2003, shows a diaper cover having a pocket for holding a urine-taking pad.

Absorbent articles utilizing a number of absorbent core components are described in U.S. Patent Publication No. 2003/0199844, published on Oct. 23, 2003 (disposable absorbent article for a lower body, having pockets to store multiple replaceable absorbent core components) and U.S. Patent Publication No. 2003/0225385, published on Dec. 4, 2003 (an absorbent article having longitudinally arranged multiple core components).

Some absorbent articles have been developed that utilize fastener elements to retain the absorbent article on a wearer. U.S. Patent Publication No. 2004/0002691, published on Jan. 1, 2004, describes absorbent pants having an optimized leg opening shape designed to transfer stress away from a fastener element and minimize the possibility of the fastener disengaging.

U.S. Pat. No. 4,936,840, issued to Proxmire on Jun. 26, 1990, describes a method of reducing waist droop in a disposable diaper. The diaper has landing zones on a front panel and ear fasteners on a back panel. The method requires the landing zones to be oriented on the front panel so tensile stresses are distributed away from leg openings and a waist opening. U.S. Patent Publication No. 2003/0220626, published on Nov. 27, 2003, describes an absorbent article that does not require a loop fastener as seen in hook and loop type fasteners.

Still other absorbent articles have been described in U.S. Pat. No. 6,520,944, issued to Jonbrink on Feb. 18, 2003 (a diaper); U.S. Patent Publication No. 2003/0229327, published on Dec. 11, 2003 (absorbent pants having high leg cuts); U.S. Patent Publication No. 2003/0164136, published on Sep. 4, 2003 (a wearing article having a wetness indicator); U.S. Patent Publication No. 2003/0149412, published on Aug. 7, 2003 (diaper having permanent leg openings); and U.S. Patent Publication No. 2003/0212378, published on Nov. 13, 2003 (a refastenable absorbent garment having elastic members at a waist opening and leg openings to enhance containment and absorption of body exudates).

None of the above inventions and patents, taken either singly or in combination, is seen to describe the instant invention as claimed. Thus a diaper with legs solving the aforementioned problems is desired.

SUMMARY OF THE INVENTION

The diaper with legs of the present invention is a lower torso garment worn by a user to retain excreted waste matter. The diaper may have fasteners to close the waist and legs, or may be of the pull-on type. The diaper includes a flat sheet wrapped around the torso with legs extending from the sides of the sheet. A front waist arch and a rear waist arch are disposed at an upper portion of the edges of the sheet. The arches extend the height of the diaper in front and back. An elastic material is disposed at the waist arches, at the junction between the legs and the central portion of the diaper, and at the end of the legs. The elastic material disposed at the end of the legs and at the junction between the legs and the central portion provide double leak protection at the legs.

These and other features of the present invention will become readily apparent upon consideration of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
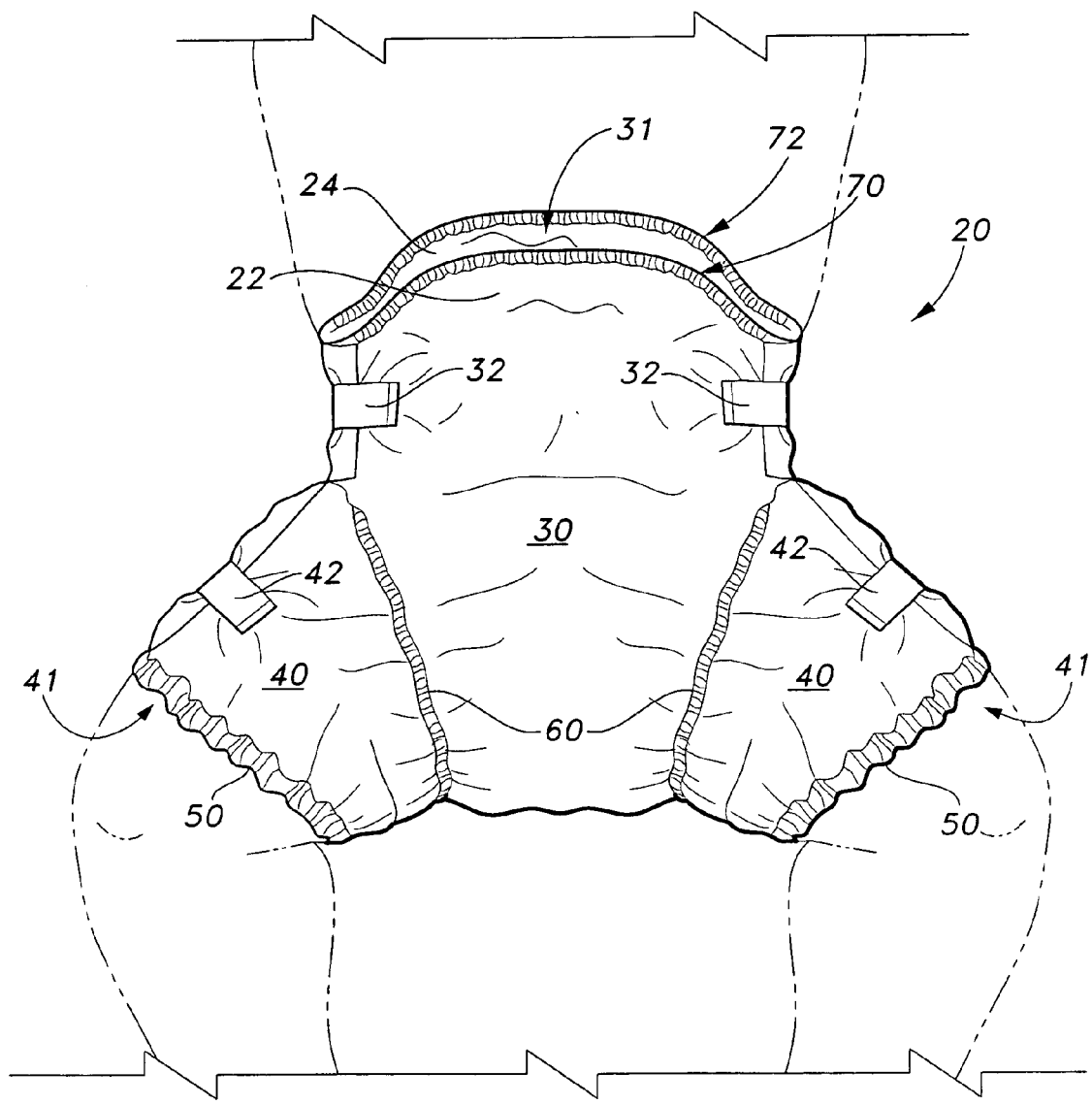
FIG. 1 is an environmental, perspective view of a diaper with legs according to the present invention.
Figure 2:
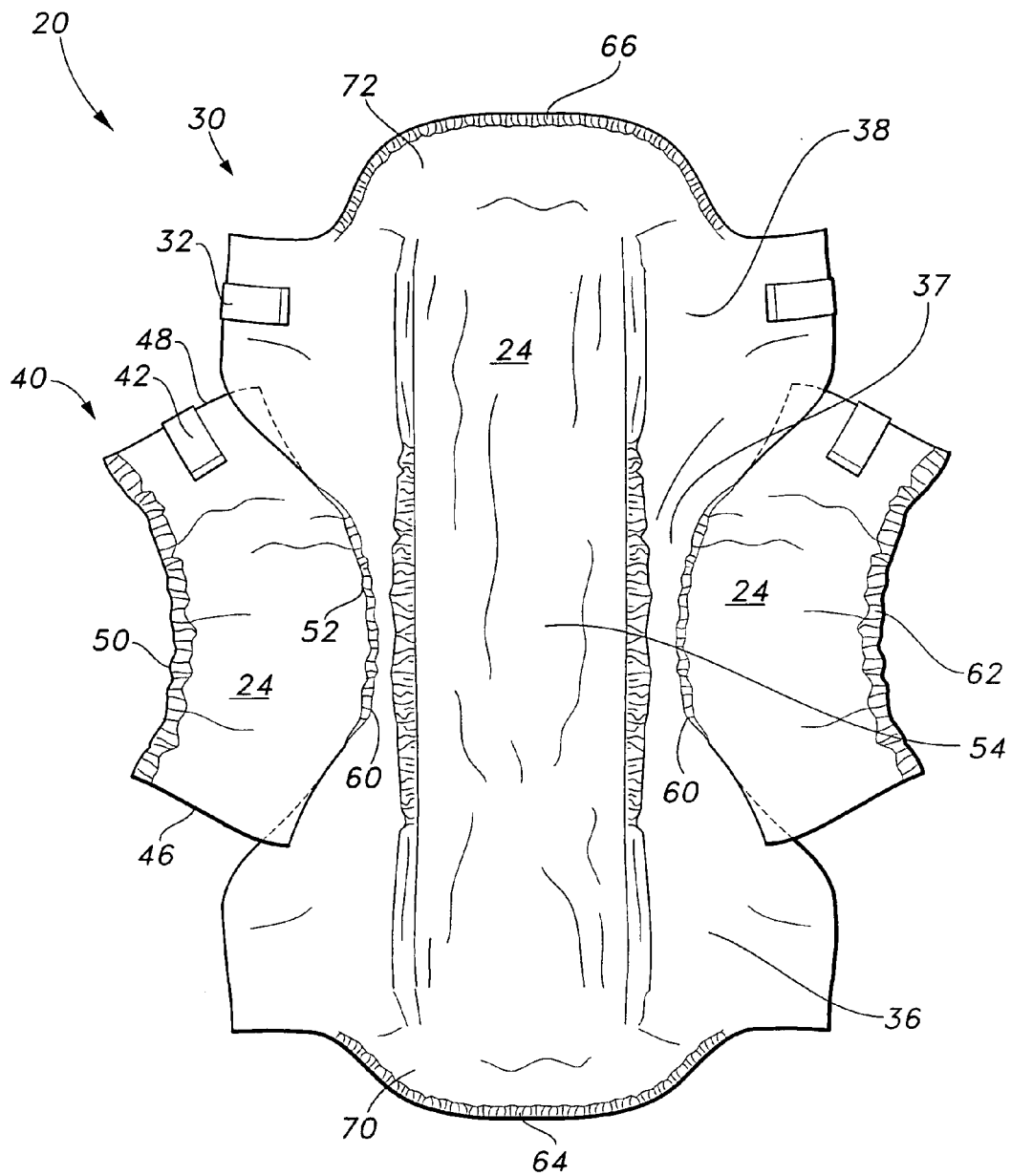
FIG. 2 is a plan view of the diaper with legs according to the present invention in an unfolded state.

The present invention is a diaper with legs, designated generally as 20 in FIGS. 1 and 2. The diaper 20 is shown in FIG. 1 in a fastened, closed configuration. The diaper 20 has a central portion 30 and legs 40. The central portion 30 has an upper portion and a lower portion that covers a user's waist and crotch. The lower region of the central portion 30 defines a pair of upper thigh openings. The upper region of the central portion 30 defines a waist opening 31. Specifically, a front waist arch 70 and a rear waist arch 72 extend from the upper region of the central portion 30 and define the waist opening 31. The arches 70, 72 elevate the waist opening 31 so the upper region of the diaper 20 covers a larger area on the user's waist.

The legs 40 downwardly depend from the pair of upper thigh openings disposed at the lower region of the central portion 30. The legs 40 have a top end and a bottom end 50. The top end of the leg sleeve 40 is attached to the central portion by elastic material 60. The bottom end 50 defines leg openings 41 that terminate on the thigh of the user's leg, preferably at about the mid to lower thigh.

The diaper 20 uses elastic material or any other resilient material to provide tight seals and conform to the user's body. For example, elastic material 60, disposed between the legs 40 and the central portion 30, forms a tight seal on the upper thigh of the user. Likewise, the bottom ends 50 of the legs 40 utilize elastic material 60 to form a tight fit on the user's mid to lower thigh.

Waste matter excreted by the user is retained within the diaper 20 due to the seal formed at the user's upper thighs by the elastic material 60. If, however, waste matter leaks past the elastic material 60, then the seal provided at the bottom end 50 of the leg sleeves 40 should contain the waste in the leg sleeves 40 and prevent waste matter from leaking out the leg openings 41. Here, the elastic material 60 and the elastic incorporated at the bottom end 50 of the leg sleeves 40 provide double protection from waste matter leaking out the leg openings 41.

The diaper 20 is maintained in the fastened, closed configuration by fastening members 32, 42. Fastening members 32 are disposed on the central portion 30 and fastening members 42 are disposed on the legs 40. The fastening members 32, 42 may be a narrow tab or a wide flap, which covers more area on the diaper 20 than the tab. At least one pair of both fasteners 32 and fasteners 42 are disposed on the diaper 20 to fasten the diaper 20 and hold it in the closed configuration. Fastener members 32, 42 are made from any reclosable fastening material.

The diaper 20 has an exterior surface and an interior surface. In the closed configuration, the interior surface 24 is dimensioned and configured to contact the user's body, crotch and legs while the exterior surface is designed to contact clothing worn by the user. The exterior surface 22 comprises non-absorbent material and is impermeable to liquids. The interior surface 24 of the diaper 20 comprises preferably two absorbent materials. The materials are two layers of absorbent liners that are disposed one on top of the other. The absorbent material gives the diaper 20 a maximum thickness of about one-half inch.

Referring now to FIG. 2, the diaper 20 is shown in an open configuration, comprising a sheet with the interior surface 24 of the diaper 20 facing upward. The central portion 30 includes a front waist panel 36, a crotch region 37 and a rear waist panel 38 forming a generally hourglass shape.

The front waist arch 70 is formed integrally with the front waist panel 36 and the rear waist arch 72 is formed integrally with the rear waist panel 38. The arches 70, 72 incorporate elastic material (e.g., gathers) 64, 66, respectively, at upper edges of the arches. Like the elastic material 60 disposed between the legs 40 and the central portion 30 and the elastic gathers incorporated at the bottom ends 50 of the legs 40, the elastic material 64, 66 disposed at the upper edges of the arches 70, 72, provides protection from leaks that otherwise would seep up the waist panels 36, 38 and out the waist opening 31.

Waist panels 36, 38, form the wide part of the diaper 20 and the crotch region 37 disposed between the waist panels 36, 38 defines the narrow part of the diaper 20. Fasteners 32 are disposed at the ends of the widest part of the rear waist panel 38. As shown in FIG. 1, the fasteners 32 hold the central portion 30 together in the closed configuration. The crotch region 37 is dimensioned and configured to cover the genitalia of the user. The crotch 37 defines the upper thigh openings of the diaper 20 and is bordered by elastic material 60. Elastic material 60 attaches the legs 40 to the central portion 30 of the diaper 20.

In the open configuration, the legs 40 have a generally rectangular panel shape defined by a rear edge 48, a front edge 46, an inner edge 52 and a bottom end 50. Fasteners 42 are disposed at the rear side 48 of the legs 40 to be refastenably affixable to the front side 46 when the legs 40 are configured around the user's legs. About a central, one-third portion of the length of the top edge 52 of each leg 40 is attached to the central portion 30 by the elastic material 60.

As mentioned above, the interior surface 24 of the diaper 20 is composed of absorbent material. In the central portion 30, the absorbent material is longitudinally arranged at the crotch region 37 to form an absorbent core 54. In the legs 40, the absorbent material is disposed within the generally rectangular panel of legs 40 between the rear edge 48, the front edge 46, the inner edge 52 and the bottom end 50.

In use, a caregiver aligns the user over the interior surface 24 of the open diaper 20 so that the user's back rests on the rear waist panel 38, the user's genitalia align with the crotch region 37, and the user's legs lie in the center of the leg sleeves 40. The diaper 20 is then folded at the crotch region 37 so the front waist panel 36 lies on the user's waist. The fastening members 32, disposed on the rear waist panel 38 can then be attached to the front waist panel 36 to hold the diaper 20 in a closed configuration.

In order to hold the waist panels 36, 38 to the user's body both panels 36, 38 must be stretched around the user's waist sides so that the fastening members 32 can be fixed to the front waist panel 36. By stretching the panels 36, 38, the elastic materials 64, 66 disposed within the arches 70, 72 are extended and the arches 70, 72 are held taut against the user's body. The arches 70, 72, therefore, create a close fit at the waist opening 31 of the diaper 20 to provide protection against waste matter leaking out of the waist opening 31.

To form the legs 40 and define the leg openings 41, the front edge 46 and the rear edge 48 are brought together and wrapped around the user's leg. Fastening member 42, disposed on the rear edge 48, stretches over and attaches to the front edge 46 forming the legs 40 and the leg openings 41. The top edges 52 of the legs 40 are free to encircle the user's legs, since only the central one-third portion of the top edges 52 are attached to the crotch 37 of the central portion 30.

Figure 3:
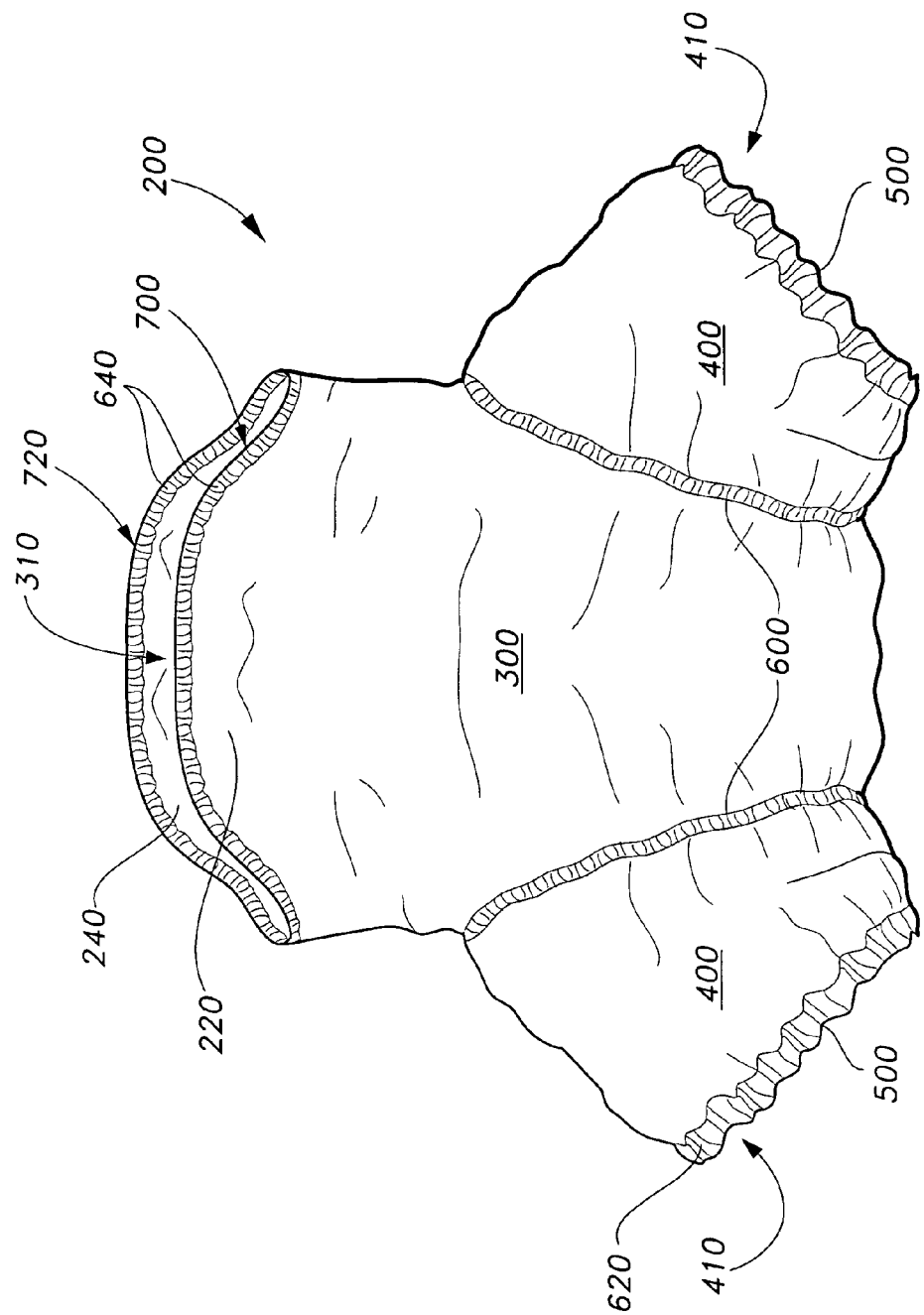
FIG. 3 is a front perspective view of an alternative embodiment of the diaper with legs of the pull-on type.

An alternative embodiment to the diaper 20 is a disposable pull-up diaper 200 shown in FIG. 3. The diaper 200 comprises a flexible, absorbent fabric having a central portion 300 having a front, a back, an upper portion defining a waist opening 310 and a lower portion to which a pair of legs 400 are attached. A front waist arch 700 and a rear waist arch 720 are disposed at the upper portion of the diaper 200, further defining the waist opening 310 and extending the coverage of the diaper 200 upward on the waist of the user. Elastic material 640 is incorporated at upper edges of the arches 700, 720 and encircles the waist of the user. The elastic material 640 forms a seal to the user's upper torso to prevent waste matter from seeping up and out the waist opening 310.

Legs 400 have a top end and a bottom end 500. The top end of the legs 400 is fixed to the lower region of the central portion 300 with elastic material 600. The bottom end 500 of the legs 400 terminate at the mid to lower thigh of the user. The legs 400 define leg openings 410. The elastic material 600 disposed between leg sleeves 400 and the central portion 300 and the elastic gather incorporated at the bottom end 500 of the legs 400 provide double leak protection against waste matter seeping down the user's leg at the leg openings 410. The diaper 200, like diaper 20, has an absorbent interior surface 240 and a non-absorbent exterior surface 220. The interior surface 240 of the diaper 200, specifically, the central portion 300 and the legs 400, preferably comprises two absorbent materials that are disposed on top of each other in layers.

It is to be understood that the present invention is not limited to the embodiments described above, but encompasses any and all embodiments within the scope of the following claims.

I claim:

1. A diaper with legs, comprising:
   a sheet of material having a central portion defining an interior surface and an exterior surface, a front waist panel, a rear waist panel and a crotch region connecting the waist panels, the waist panels defining a waist opening, the crotch region defining a pair of thigh openings;
   two legs attached to the thigh openings of the central portion, each said leg comprises a rectangular panel having a front edge, a rear edge, an inner edge joined to the central portion, and a bottom end adapted to form leg openings;
   elastic material disposed between the legs and at least a portion of the thigh openings;
   a front waist arch integral with and extending from the front waist panel and having an upper edge; and
   a rear waist arch integral with and extending from the rear waist panel and having an upper edge;
   whereby, the arches extend the waist opening upward on a user's torso and the legs extend the diaper downward on the user's legs to provide protection from waste matter that may leak up the user's waist or down the user's legs.

2. The diaper with legs according to claim 1, further comprising elastic material incorporated into the upper edge of the front waist arch.

3. The diaper with legs according to claim 1, further comprising elastic material incorporated into the upper edge of the rear waist arch.

4. The diaper with legs according to claim 1, further comprising at least one pair of fasteners disposed on the rear waist panel for fixing said rear waist panel to the front waist panel.

5. The diaper with legs according to claim 1, wherein the elastic material extends for a central one-third portion of the legs and thigh openings.

6. The diaper with legs according to claim 1, further comprising at least one pair of fasteners disposed on the rear edge of the panel for fastening the rear edge to the front edge to define the legs.

7. The diaper with legs according to claim 1, further comprising absorbent material disposed between the interior surface of said central portion and each said leg and the exterior surface of said central portion and each said leg.

8. The diaper with legs according to claim 7, wherein said absorbent material further comprises an absorbent core longitudinally arranged in the central portion.

9. The diaper with legs according to claim 7, wherein said absorbent material comprises two layers of absorbent material.

10. The diaper with legs according to claim 1, further comprising releasable fasteners securing said front waist panel and said rear waist panel in order to define the waist opening and securing each said leg together.

11. The diaper with legs according to claim 1, wherein said front waist panel is permanently secured to said rear waist panel in order to form a pull-on diaper.

12. The diaper with legs according to claim 1, further comprising an elastic gather disposed around each of the leg openings.

13. The diaper with legs according to claim 1, wherein the elastic material is disposed about the entire inner edge of each said leg.

* * * * *